United States Patent
Simmonds et al.

(10) Patent No.: US 6,253,615 B1
(45) Date of Patent: *Jul. 3, 2001

(54) METHOD AND APPARATUS FOR IN SITU MEASUREMENTS OF CORROSION OF SUBMERGED SURFACES

(75) Inventors: Kirth E. Simmonds, Clinton, MD (US); Narendra K. Batra, Springfield, VA (US); Richard B. Mignogna, La Plata, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,130

(22) Filed: Jun. 30, 1999

Related U.S. Application Data

(63) Continuation of application No. 09/053,075, filed on Apr. 1, 1998, now Pat. No. 5,942,687.

(51) Int. Cl.[7] .............................. G01H 1/00; G01N 29/00
(52) U.S. Cl. ................................. 73/579; 73/600; 73/623
(58) Field of Search ............................... 73/86, 597, 598, 73/618, 623, 630, 579, 67.8, 602, 599, 600; 702/33, 34, 35, 39

(56) References Cited

U.S. PATENT DOCUMENTS

| | | | |
|---|---|---|---|
| 4,512,194 | * | 4/1985 | Beuter ..................................... 73/602 |
| 4,912,683 | * | 3/1990 | Katahara et al. ....................... 367/25 |
| 5,205,174 | * | 4/1993 | Silverman et al. .................... 73/623 |
| 5,456,114 | * | 10/1995 | Liu et al. ............................... 73/597 |
| 5,554,808 | * | 9/1996 | Chiao ..................................... 73/598 |
| 5,635,645 | * | 6/1997 | Ottes et al. ............................. 73/623 |
| 5,929,349 | * | 7/1999 | Bass et al. ........................... 73/865.8 |
| 5,942,687 | * | 8/1999 | Simmonds et al. .................... 73/623 |
| 5,955,669 | * | 4/1985 | Egami ................................... 73/602 |

* cited by examiner

Primary Examiner—Helen Kwok
(74) Attorney, Agent, or Firm—John J. Karasek; Jane B. Marciniszyn

(57) ABSTRACT

An aspect of the present invention is an apparatus for inspecting a base of a liquid filled tank for corrosion, having (a) a housing for use in the liquid filled tank; (b) a set of one or more ultrasonic transducers mounted to the housing, for directing one or more ultrasonic pulses at the base, where the ultrasonic pulses each have a frequency selected to produce a return signal from the base, and for receiving this return signal; and (c) a data capturing system for storing information from these return signals. Optional features include a second set of one or more ultrasonic transducers for directing one or more ultrasonic pulses at the liquid/gas interface at a frequency selected to produce a return signal from the liquid/gas interface, a data analysis system, a locomotive system, and a spatial location system. Another aspect of the invention is a method for inspecting a base of a liquid filled tank for corrosion, having the steps: (a) directing a broadband ultrasonic pulse at the base from an ultrasonic transducer within the tank, where the ultrasonic pulse includes a resonant frequency for the tank base over the range of expected thicknesses for the base; (b) receiving a return signal with the ultrasonic transducer; (c) performing a Fourier analysis on the return signal to generate a frequency domain signal; and (d) determining the thickness of the base from the frequency domain signal.

24 Claims, 5 Drawing Sheets

METHOD AND APPARATUS FOR IN SITU MEASUREMENTS OF CORROSION OF SUBMERGED SURFACES

CROSS-REFERENCE TO TELATED APPLICATION

This is a continuation of application Serial No. 09/053,075, filed on Apr. 1, 1998, now issued as U.S. Pat. No. 5,942,687.

BACKGROUND OF THE INVENTION

1. Field of the Invention

The present invention relates generally to monitoring liquid storage tanks for corrosion. More particularly, the present invention relates to a novel apparatus and method for the in situ monitoring such tanks for thinning (due to corrosion) of the tank bottom, and optionally for uneven settling of the tank, using ultrasonic transducers mounted on a mobile robotic device for use inside liquid filled tanks.

2. Description of the Related Art

With respect to storage tanks.

Large metal storage tanks are used to store a variety of liquids, including especially water, petroleum, and petroleum products. These tanks, which are commonly made from non-stainless steel plates, are subject to corrosion and eventual failure over time. Even tanks that are intended to store only petroleum and petroleum products almost inevitably will have a substantial amount of water in them, greatly aggravating their tendency to oxidize. Thus, it is necessary to periodically inspect these tanks, and to make repairs before such failure. However, because of the enormous size of these tanks, it is expensive and inconvenient to empty a tank each time it is to be inspected.

Typical tanks for petroleum products are made from ¼" to ½" thick steel plates welded together. They are commonly hundreds of feet tall and hundreds of feet in diameter. They are usually built above ground, but may also be made at least partially below ground. If such a tank should fail while filled with product, the environmental damage would be staggering.

Complicating the inspection process is the presence of sediment in the tanks. At the bottom of most liquid storage tanks there is a layer of sediment including rust, dirt, debris, petroleum solids, etc. This layer may be anywhere from several millimeters to several feet thick. An effective tank inspection system must either be able to see through this sediment, or must be able to displace the sediment to allow for direct inspection.

Bilges of large ships (e.g., aircraft carriers tankers) likewise must be inspected periodically for corrosion. Many of the same concerns are raised for the inspection of bilges as are raised for the inspection of tanks.

With respect to corrosion monitoring systems.

Available systems for monitoring liquid filled tanks for corrosion suffer from any of several common shortcomings.

One problem that has not been satisfactorily addressed by the art has been the difficulty of using ultrasonic probes to obtain reflection signals from both the top and bottom surfaces of the base plate of a tank. The sediment layer described above scatters ultrasonic waves, dramatically attenuating these waves, and thereby decreasing their ability to penetrate the bottom steel plate. Moreover, ultrasonic waves scattered from the sediment are a source of noise that present systems do not adequately address.

U.S. Pat. No. 5,205,174, issued Apr. 27, 1993 to Silverman et al. (Silverman '174) is representative. This patent teaches the use of ultrasonic transducers for inspecting the bottom surfaces of storage tanks. This system teaches the use of very high frequency ultrasonic pulses (about 15.4 MHz, with a wavelength of 0.0156"). Such high frequency pulses will be so diminished in amplitude that signal detection would be problematic at best. This is particularly true if the ultrasonic pulse is scattered by plate surface that has been roughened by corrosion and attenuated by a layer of sediment. Silverman '174 attempts to mitigate the former problem by including a cleaning system in the apparatus, to remove sediment from the bottom as the apparatus moves along. In principle, this system would work by scrubbing and vacuuming the base free of sediment, irrigating a the base with a stream of clean fluid to remove any remaining sediment, and filtering out the sediment so that it is not returned to the tank. At best, this is a very complicated system that does not address the problem of scattering by a surface that has been roughened by corrosion.

SUMMARY OF THE INVENTION

Accordingly, it is an object of this invention to provide detailed information on tank bottom thickness.

It is a further object of this invention to provide such information even for heavily corroded liquid storage tanks.

It is a further object of the invention to provide such information even for liquid storage tanks having a layer of sediment on the bottom.

These and additional objects of the invention are accomplished by the structures and processes hereinafter described.

An aspect of the present invention is an apparatus for inspecting a base of a liquid filled tank for corrosion, having (a) a housing for use in the liquid filled tank; (b) a set of one or more ultrasonic transducers mounted to the housing,.for directing one or more ultrasonic pulses at the base, where the ultrasonic pulses each have a frequency selected to produce a return signal from the base, and for receiving this return signal; and (c) a data capturing system, for storing information from these return signals. Optional features include a second set of one or more ultrasonic transducers for directing one or more ultrasonic pulses at the liquid/gas interface at a frequency selected to produce a return signal from the liquid/gas interface, a data analysis system, a locomotive system, and a spatial location system.

Another aspect of the invention is a method for inspecting a base of a liquid filled tank for corrosion, having the steps: (a) directing a broadband ultrasonic pulse at the base from an ultrasonic transducer within the tank, where the ultrasonic pulse includes a resonant frequency for the tank base over the range of expected thicknesses for the base; (b) receiving a return signal with the ultrasonic transducer; (c) performing a Fourier analysis on the return signal to generate a frequency domain signal; and (d) determining the thickness of the base from the frequency domain signal.

BRIEF DESCRIPTION OF THE DRAWINGS

A more complete appreciation of the invention will be obtained readily by reference to the following Description of the Preferred Embodiments and the accompanying drawings in which like numerals in different figures represent the same structures or elements. wherein.

DETAILED DESCRIPTION OF THE PREFERRED EMBODIMENTS

With respect to the overall system of the invention.

Figure 1:
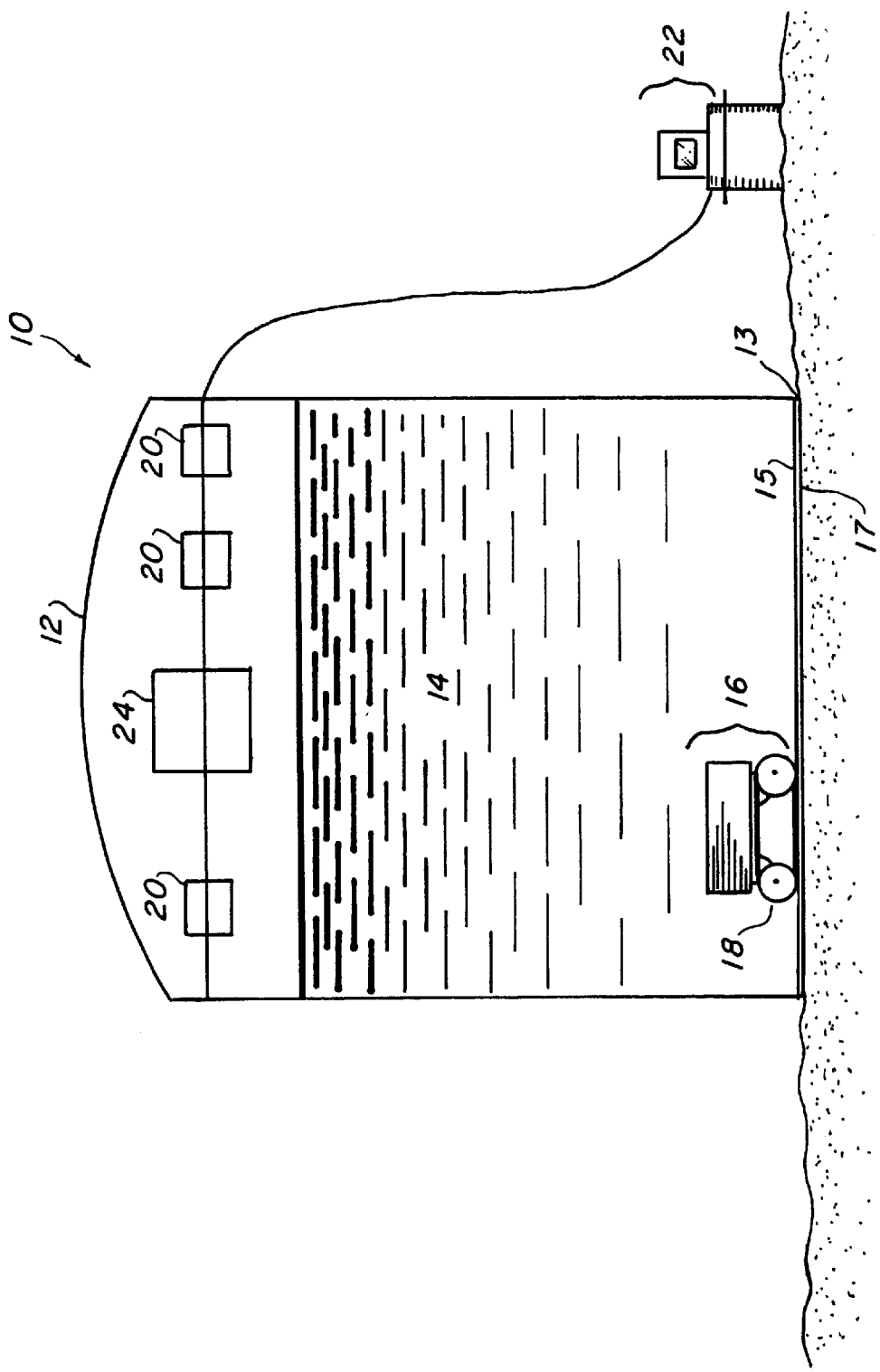
FIG. 1 shows a schematic of the system according to the invention.

Referring to FIG. 1, this shows a schematic of the system 10 according to the invention. A tank 12 is filled with a liquid inventory 14, such as a fuel. The tank 12 has a base 13 typically made of welded steel plates. The system of the invention is preferably designed to image the top 15 and bottom 17 surfaces of the tank base 13. Inside the tank 12 is a remote, automated device 16 housing the ultrasonic transducers (not shown), and the propulsion system 18 (shown here as a motor-driven track device). Also shown (typically inside the tank) are location transmitters 20 in communication with the device 16, for locating the device 16 within the tank 12. The mobile device 16 is typically connected to a data collection and analysis system 22 (typically a programmed digital computer). These connections typically are through a telemetry system (not shown), but alternatively may be through cabling. A microwave power source 24 preferably is used to power the device 16. Alternatively, cabling or large capacity on-board batteries or fuel cells are used to power the device. These power sources may also be used in conjunction with one another. e.g., batteries used as the principal power source during operations, and a microwave power source used to recharge the batteries, and also for additional power during operation.

Propulsion systems may be bottom-drive systems (such as the track drive system shown), or free-swimming systems, such as propeller or jet driven systems.

With respect to the transducers of the invention.

Figure 2:
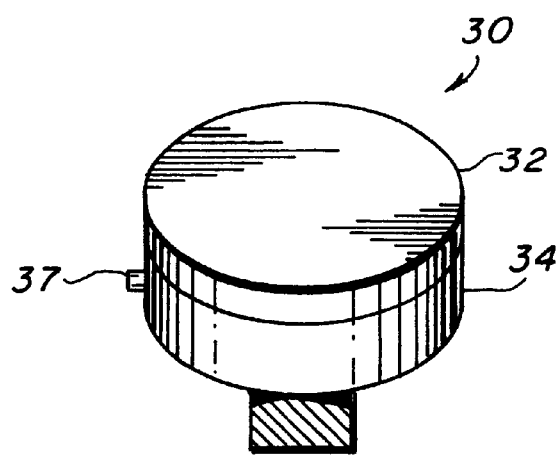
FIG. 2 shows an elevation of a transducer according to the invention.

Referring to FIG. 2, this shows an elevation of a typical ultrasonic transducer 30 used according to the invention. Typical transducers used according to the invention will have a piezoelectric element 32 (usually PZT), mounted in a housing 34 that contains the electrodes coupled to the piezoelectric element 32, for driving the element. Typically, the housing 34 also has the contact 37 for electrically connecting the transducer to the console housing the pulse generator and data collection and analysis system (not shown).

Figure 3:
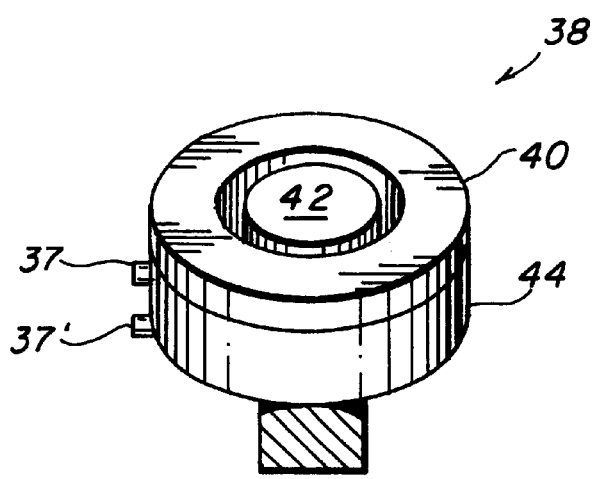
FIG. 3 shows an elevation of another transducer according to the invention.

Referring to FIG. 3, this shows a preferred ultrasonic transducer 38 used according to the invention. This transducer has separate piezoelectric elements for transmitting 40 and receiving 42. The two piezoelectric elements 40, 42 are mounted in a housing 44 that contains the electrodes coupled to the piezoelectric elements 40, 42. Preferably, the two elements are coaxial. Preferably, the receiving element has a smaller diameter than the transmitting element—the smaller diameter will permit the receiving element to receive a signal integrated over a smaller area, leading to better spatial resolution. Contacts 37, 37' electrically connect the two elements to the console housing the pulse generator and data collection and analysis system (not shown).

Figure 4:
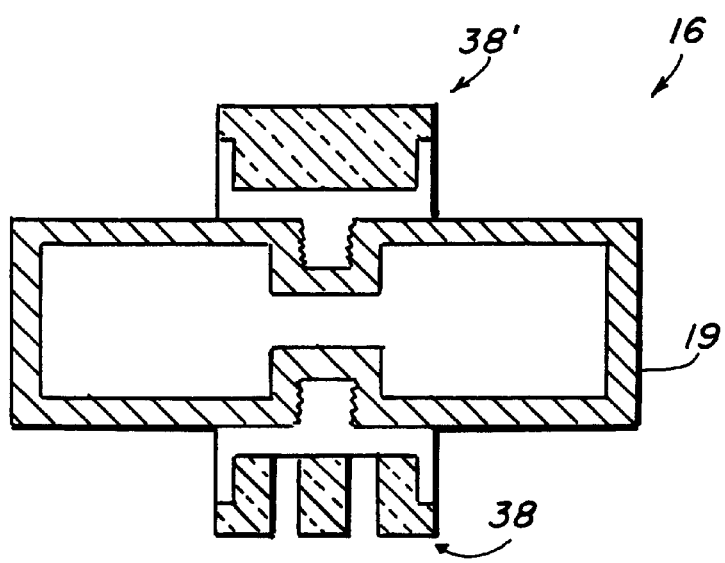
FIG. 4 shows a detailed section of a system according to the invention.

The system of the invention will include at least one set of transducers, and preferably two sets of transducers (for illustration purposes, a single transducer is sometimes shown and referred to herein as representative of a set of transducers). As shown in FIG. 4, the first transducer 38 will be directed toward the base of the tank (typically on the bottom of the housing 19), for imaging the bottom plate of the tank. The optional second transducer 38' will be directed toward the top of the tank (typically on the top of the housing 19), for measuring the height of the liquid.

The configurations and operating frequencies of the two transducers need not be the same, since they perform different functions.

The first transducer 38 should be configured to generate a signal from the top 15 and bottom 17 surfaces of the tank base 13. This will entail transmitting a pulse that can penetrate a highly attenuating layer of sediment on the tank floor, and reflect a portion of the pulse back off the top surface. It will further entail transmitting enough of the remaining portion of the pulse to the bottom surface (despite typical further scattering by the corroded top surface of the base and attenuation through the steel plate) so that energy can reflect off the bottom surface of the steel plate. It has been discovered that the frequencies taught in the art (in particular, the frequencies taught in the previously cited Silverman '174) are far too high to successfully generate a useful return signal off both the corroded top and bottom surfaces of the steel base plate. It has been discovered that frequencies between approximately 0.5 MHz and 2.0 MHz are preferred, and that a frequency of about 1.0 MHz is more preferred for a base plate of about ¼" thickness. Skilled practitioners will recognize that if the pulse frequency is too low, the spatial resolution of the signal will be reduced beyond a point that is acceptable.

The second transducer 38' should be configured to generate a signal from the top surface of the liquid in the tank 14. Because spatial resolution will be more critical for imaging the bottom plate than for imaging the liquid surface, using a less expensive single element transducer 30 should be acceptable.

Figure 5:
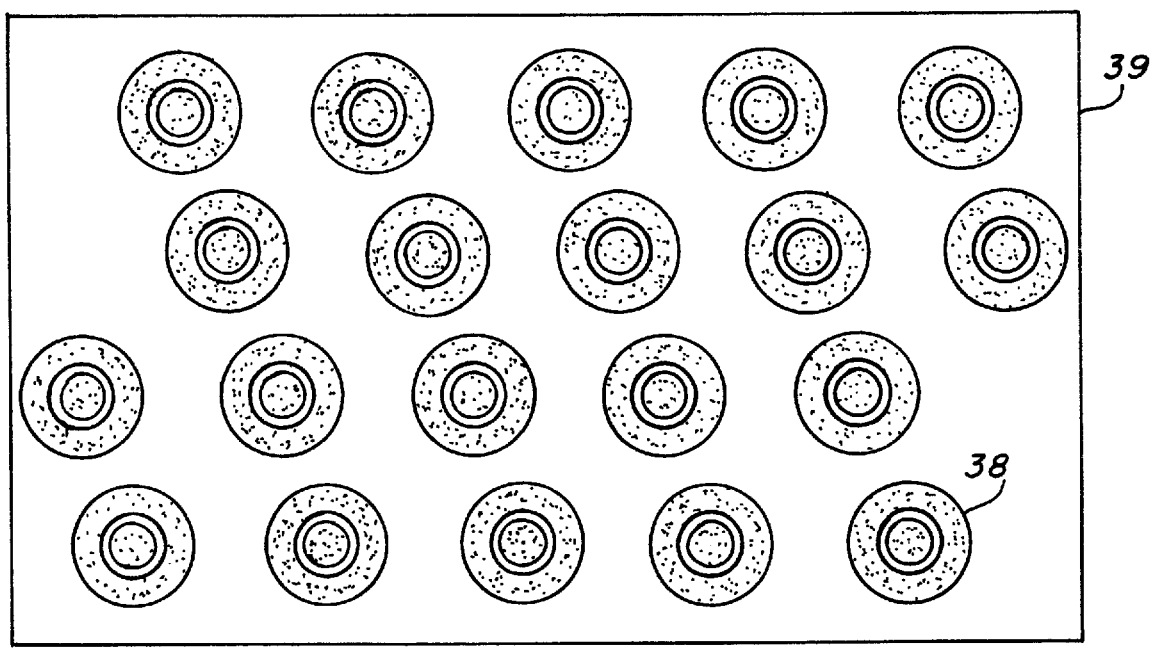
FIG. 5 shows a view of an array of transducers according to the invention.

Rather than using a single transducer to image in a given direction, it is preferred to use an array of transducers, to provide imaging over a wide swath of the tank bottom with each pass of the probe. A simple 1-dimensional array of multiplexed transducers will speed up imaging over the tank bottom, for instance. Preferably, as shown in FIG. 5, a 2-dimensional array of transducers is used. As shown, an array 39 of transducers 38 may be arranged so that each transducer will yield information about a given portion of a path of a given width over which the array passes.

With respect to the electronic system.

Figure 6:
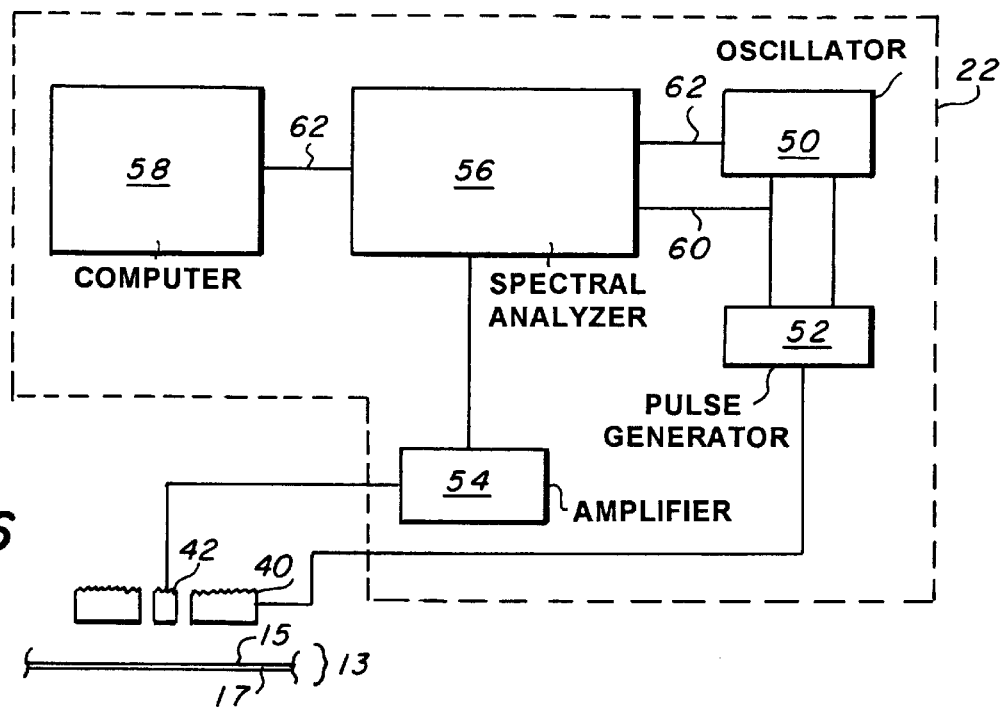
FIG. 6 shows a schematic of an electronic system according to the invention.

Referring to FIG. 6, this schematically depicts an exemplary system according to the invention. An oscillator 50 provides timing for the system. A pulse generator 52 coupled to the oscillator transmits regularly timed broadband ultrasonic pulses to the transducer. A typical commercially available pulse generator will have built-in amplification. In response to a pulse, the transducer transmitter 40 transmits a broadband ultrasonic pulse. The transducer receiver 42 receives a return signal, which it transmits to an amplifier 54. The amplifier 54 amplifies the return signal, and transmits the amplified return signal to a temporal tracking and spectral analyzer 56, that samples the return signal, performs a Fourier analysis on a gated portion of the return signal, and transmits the Fourier analysis data to a computer for data processing and image display 58. A synchronization lead 60 sends a synchronization signal to the temporal tracking and spectral analyzer 56, to provide synchronization. An interface bus 62, typically a general purpose interface bus, connects the computer 58, the temporal tracking and spectral analyzer 56, and the pulse generator 52, to provide data transfer and control.

A console 22 typically houses the oscillator 50, pulse generator 52, computer 58, spectral analyzer 56, and amplifier 54.

Figure 6A:
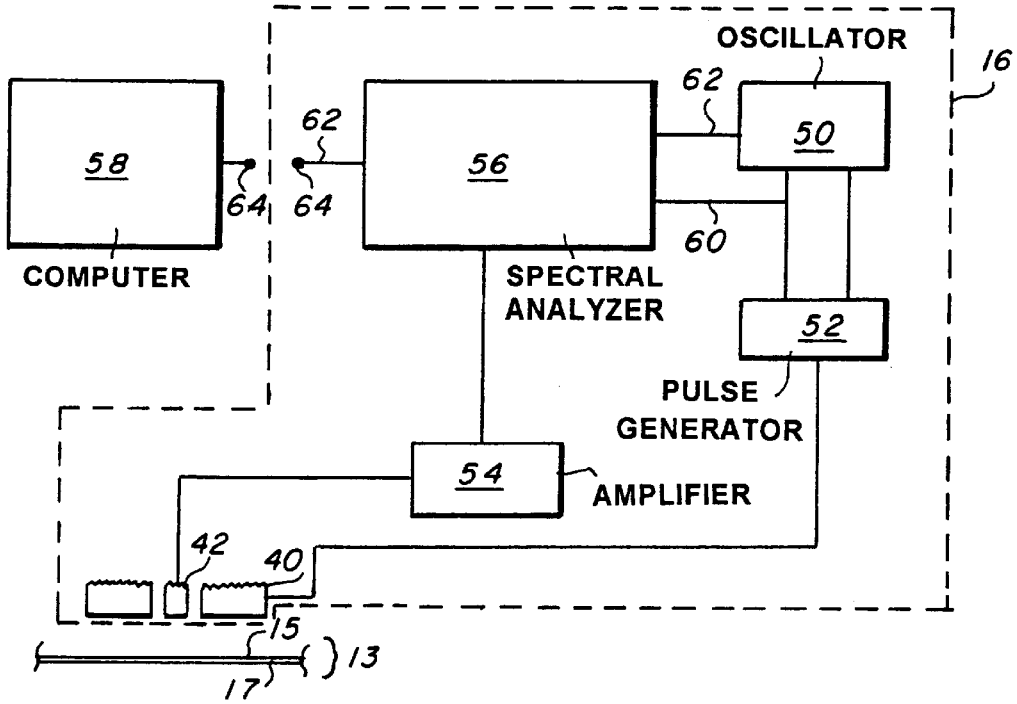
FIG. 6A shows a schematic of another electronic system according to the invention.

Alternatively, as shown in FIG. 6A, remote, automated device 16 houses most of these electronic components, and microwave transceivers 64 are used for communication between the computer 58 and the device 16.

The optimal gated return signal sampled will depend on the pulse length of the transmitted signal and the transmission time through the liquid medium. It is desired to sample only the portion of the return signal that does not include the pulse output from the transducer or the reflection from the top surface of the tank base. Morever, the gated return signal should not include the subsequent reflections. It has been found that for pulse lengths of about 2 $\mu$s, gate lengths that are between about two and about ten times the pulse length work well in the present invention.

As noted, the peak frequency will be inversely proportional to the thickness of the bottom plate. The relationship between the thickness and the peak frequency is given by $v=c/\lambda$, where $v$ is the peak frequency, c is the propagation velocity of the ultrasonic waves in the tank bottom material, and $\lambda$ is the wavelength of the first harmonic, which will be proportional to the tank bottom thickness. However, it may be that the absolute propagation velocity is not known for a given tank bottom. If the propagation velocity is not known absolutely, then the absolute tank bottom thickness at a given point cannot be determined. However, a relative thickness may be determined. For instance, all the tank bottom thicknesses may be normalized to (expressed as a fraction of) the maximum thickness (corresponding to the point on the tank bottom with the lowest peak frequency). Typically, this map of the normalized tank bottom thickness will be sufficient to achieve the objects of the invention. Alternatively, an estimate of the propagation velocity may be used.

With respect to the propulsion system.

A number of propulsion systems are suitable for use in the present invention. For example, a track system 18 will work well in most types of tanks. See Silverman '174, incorporated by reference herein. Other systems that should work include propulsion systems using propellers and propulsion systems using liquid jets.

With respect to the positioning system.

Several positioning systems are suitable for use in the present invention. As discussed supra, several positioning transmitters may be positioned within the tank, and the device may triangulate a position from these transmitters, similar to what is done with the global positioning system. Alternatively, an inertial navigational system and/or an active sonar system may be used to monitor the position of the device. Temperature correction may be used to enhance the precision of an active sonar locating system.

With respect to the mapping system.

Thickness data preferably is correlated with positional data collected from the positioning system, to produce a map of the tank bottom. This map may be displayed in any suitable manner, e.g., as a color plot with different colors representing different bottom thicknesses, as a contour plot, grayscale plot, or as a three dimensional bar or line plot.

Having described the invention, the following examples is given to illustrate specific applications of the invention, including the best mode now known to perform the invention. This specific examples is not intended to limit the scope of the invention described in this application.

EXAMPLE 1

Measurement of Aluminum Plate Thickness for Sample Not Covered by Sediment

Figure 7:
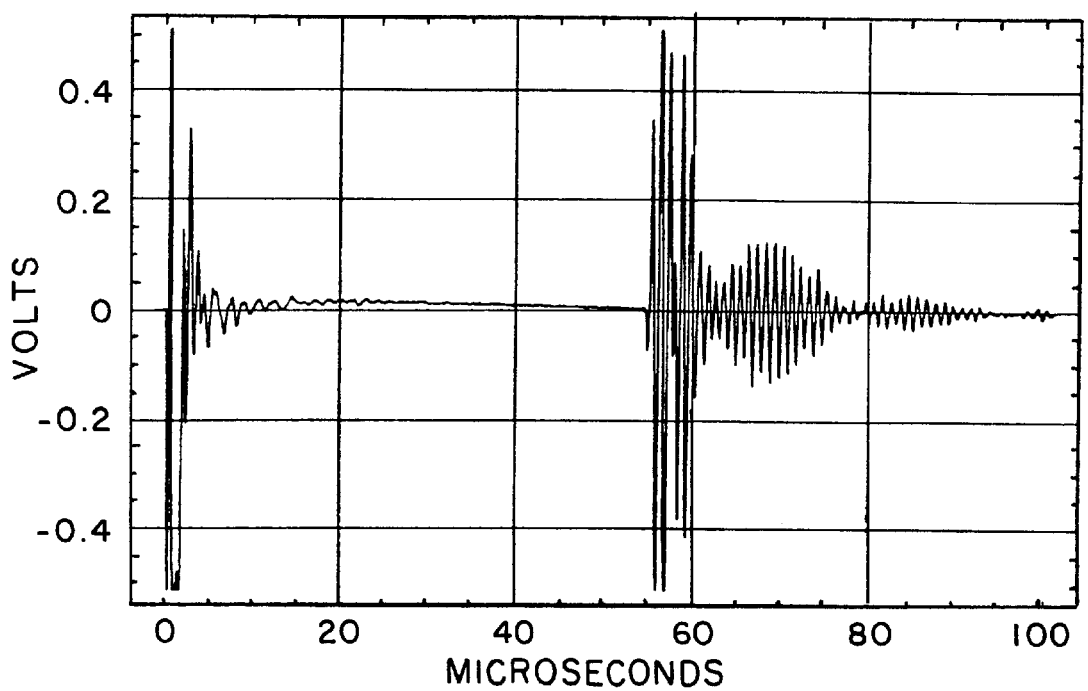
FIG. 7 shows a time domain plot of a transducer signal in a method according to the invention.

An aluminum sample having stepped thicknesses ranging from 0.52 cm to 1.31 cm was placed in a small tray of water. A custom-built ultrasonic transducer was placed in the tank, and aimed at a portion of the aluminum plate having a known thickness of 0.65 cm, from a distance of about 5 cm. The transducer was connected to an analysis unit comprising a Tektronix DSA602A Digitizing Signal Analyzer, a Metrotek Pulser Model MP215 (or, in some experiments, a Stanford Research Model DG535 Four Channel Digital Delay/Pulser Generator and ENI Power Amplifier Model 325LA), a Metrotek Receiver Model MR101 (or a Matec Broadband Receiver Model 605), a Metrotek Scanner and Controller Model C403, and a Panametrics 1 MHz broadband transducer (or Valpey-Fisher special order 1 MHz broadband annular array transducer), configured as shown in FIG. 6. A broadband ultrasonic pulse having a center frequency $v_{center}=1.0$ MHz and a bandwidth of approximately from 0.8 MHz to 1.5 MHz (full width at half maximum) was transmitted to the steel plate. The time domain signal received by the transducer is shown in FIG. 7. As seen in FIG. 7, the broadband output pulse lasted about 5 $\mu$s (from t=0 to about t =about 5 $\mu$s). The ultrasonic pulse reflected from the front surface of the Al plate, generating a high intensity return signal for about 10 $\mu$s, from about (from about t=55 $\mu$s to about t=65 $\mu$s). After about 65 $\mu$s, the return signal had a reduced intensity. The next 20 $\mu$s (from about t=65 $\mu$s to about t=85 $\mu$s) was taken as the resonant return signal, and was gated for Fourier analysis.

Figure 8:
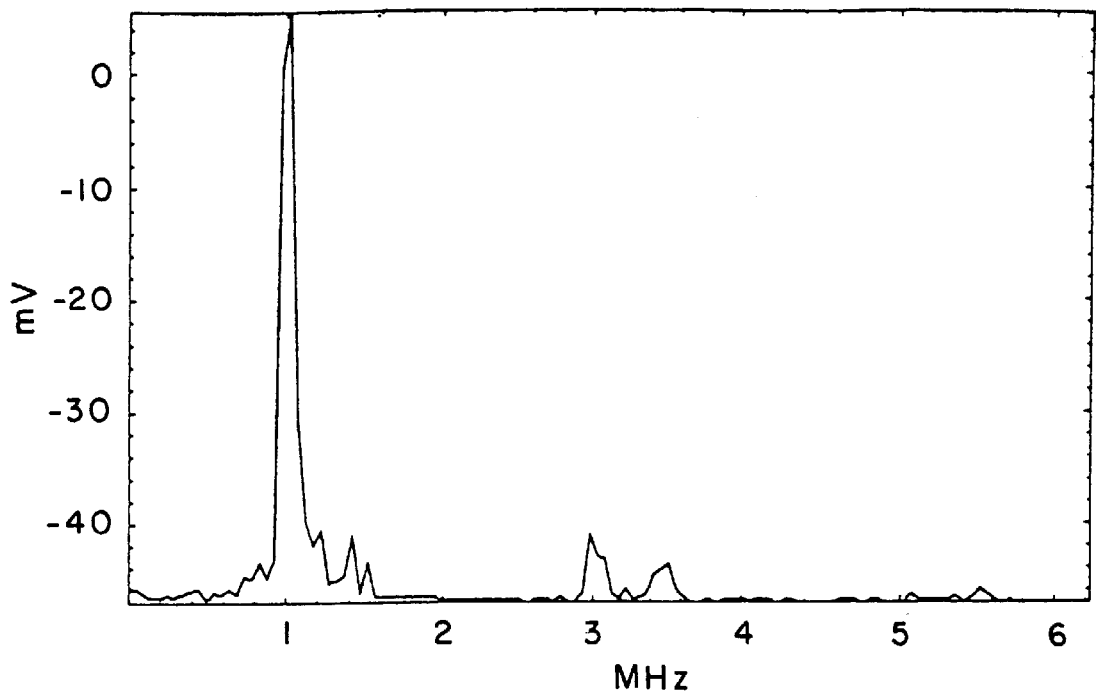
FIG. 8 shows a frequency domain plot of a gated portion of the time domain signal depicted in FIG. 7.

A fast Fourier transform was performed on the gated portion of the return signal, with the results shown in FIG. 8. The peak frequency is associated with the thickness of the plate, as discussed supra.

Obviously, many modifications and variations of the present invention are possible in light of the above teachings. It is therefore to be understood that, within the scope of the appended claims, the invention may be practiced otherwise than as specifically described.

What is claimed is:

1. A method for inspecting a submerged plate for corrosion, comprising the steps:

(a) directing an ultrasonic pulse at a first position on said submerged plate from a first ultrasonic transducer, wherein said ultrasonic pulse has a frequency selected to produce a return signal including reflections from both a proximal surface of said submerged plate and a distal surface of said submerged plate;

(b) receiving said return signal with said first ultrasonic transducer;

(c) performing a Fourier analysis on said return signal to generate a first transducer frequency domain signal; and (d) determining a thickness for said submerged plate at said first position from said first transducer frequency domain signal.

2. The method of claim 1, wherein said frequency is between about 0.5 MHz and about 2.0 MHz.

3. The method of claim 1, wherein said frequency is selected to generate a reflection through said submerged plate wherein said submerged plate comprises at least ¼" steel.

4. The method of claim 3, wherein said steel is non-stainless steel.

5. The method of claim 4, wherein said steel is corroded steel.

6. The method of claim 1, wherein said first position is at a known position on said submerged plate.

7. The method of claim 6, wherein said method further comprises the steps of:
   (e) translating said first ultrasonic transducer to at least one different positions on said submerged plate; and
   (f) at each of said positions, performing steps (a) through (d).

8. The method of claim 7, wherein said method further comprises the step of:
   (g) storing said thickness for each of said positions as a map of said submerged plate.

9. The method of claim 1, wherein said method further comprising the steps of:
   (h) directing a surface-directed ultrasonic pulse to a first position at a liquid surface from a second ultrasonic transducer, wherein said surface-directed ultrasonic pulse has a frequency selected to produce a second transducer surface return signal including a reflection from said liquid surface;
   (i) receiving said surface return signal with said second ultrasonic transducer;
   (j) analyzing said surface return signal in the time domain, to generate a second transducer time domain signal; and
   (k) determining a distance from said second transducer to said first position at said liquid surface from said frequency domain signal.

10. The method of claim 9, wherein said frequency of said pulse from said second transducer is between about 100 kHz and about 10 MHz.

11. The method of claim 9, further comprising the steps of;
   (l) determining a distance from said first transducer to said proximal surface of said submerged plate at said first position from said first transducer; and
   (m) determining a liquid height at said first position from said distance from said first transducer to said proximal surface of said submerged plate at said first position, said distance from said second transducer to said first position at said liquid surface, and a distance between said first transducer and said second transducer.

12. The method of claim 11, further comprising the steps of:
   (n) translating said first and second ultrasonic transducers to at least one different position on said plate;
   (o) at a plurality of said different positions, performing steps (a) through (d), steps (h) through (k), and steps (l) and (m); and
   (p) storing liquid heights for each of said positions as a map of said liquid heights.

13. The method of claim 1, wherein said submerged plate is a plate in a liquid storage tank.

14. The method of claim 13, wherein said storage tank is a storage tank for water, petroleum, or gasoline.

15. An apparatus for inspecting a submerged plate for corrosion, comprising:
   means for directing an ultrasonic pulse at a first position on said submerged plate from a first ultrasonic transducer, wherein said ultrasonic pulse has a frequency selected to produce a return signal including reflections from both a proximal surface of said submerged plate and a distal surface of said submerged plate;
   means for receiving said return signal with a first ultrasonic transducer;
   means for performing a Fourier analysis on said return signal to generate a first transducer frequency domain signal; and
   means for determining a thickness for said submerged plate at said first position from said first transducer frequency domain signal.

16. The apparatus of claim 15, wherein said frequency is between about 0.5 MHz and about 2.0 MHz.

17. The apparatus of claim 15, wherein said first transducer is a composite transducer having a transmit portion and a receive portion, said transmit and receive portions arranged concentrically and said receive portion being smaller than said transmit portion.

18. The apparatus of claim 17, wherein said receive portion is not larger than about ¼" in diameter.

19. The apparatus of claim 15, further comprising an analysis system adapted for performing a Fourier analysis on said return signal to generate a first transducer frequency domain signal and determining a thickness for said submerged plate from said first transducer frequency domain signal.

20. The apparatus of claim 15, further comprising:
   a second ultrasonic transducer mechanically coupled to a housing for directing a surface-directed ultrasonic pulse at a liquid surface and for receiving said surface return signal, wherein said surface-directed ultrasonic pulse has a frequency selected to produce a surface return signal including a reflection from said liquid surface; and
   a data capturing system adapted for storing said surface return signal from said liquid surface.

21. The apparatus of claim 20, further comprising an analysis system adapted for performing a Fourier analysis on said return signals from said first and second ultrasonic transducers to generate a first transducer frequency domain signal and a second transducer frequency domain signal, and for determining a thickness for said submerged plate from said first transducer frequency domain signal and a distance to said liquid surface from said second transducer frequency domain signal.

22. The apparatus of claim 15, wherein said first ultrasonic transducer is an element in an array of ultrasonic transducers for directing ultrasonic pulses at said submerged plate and for receiving said return signal, wherein said ultrasonic pulses have frequencies selected to produce return signals including reflections from both said proximal surface of said submerged plate and said distal surface of said submerged plate.

23. The apparatus of claim 15, wherein said submerged plate is a plate in a liquid storage tank.

24. The apparatus of claim 23, wherein said storage tank is a storage tank for water, petroleum, or gasoline.

* * * * *